United States Patent [19]

Childers, Jr. et al.

[11] Patent Number: 4,873,331

[45] Date of Patent: Oct. 10, 1989

[54] NORADAMANTYL-CARBOXYLIC ACID PIPERAZINOALKYL ESTERS

[75] Inventors: Wayne E. Childers, Jr., Yardley; Magid A. Abou-Gharbia, Glen Mills, both of Pa.

[73] Assignee: American Home Products Corporation, New York, N.Y.

[21] Appl. No.: 282,711

[22] Filed: Dec. 9, 1988

[51] Int. Cl.$^4$ .................. C07D 401/04; C07D 403/04; C07D 295/06; C07D 295/08
[52] U.S. Cl. .................... 544/295; 544/357; 544/360; 544/394
[58] Field of Search .............. 544/295, 357, 360, 394, 544/399, 380; 514/255, 252

[56] References Cited

U.S. PATENT DOCUMENTS 4,202,898  5/1980  Depoortere .................. 544/394

FOREIGN PATENT DOCUMENTS 7017031  5/1971  Netherlands .

OTHER PUBLICATIONS

Derwent Abstract 85000957/01—New 1-pyrimidyl-4-substd.piperazine derivs. with CNS e.g. anxiolytic and antidepressant activities —12/20/84.
Barone et al., Drug Clin. Pharm., 20, 770, 1986.
Derwent Abstract 87-049798/07—Treatment of Sexual Dysfunction by (pref. oral) Administration of Buspirone—2/3/87.

*Primary Examiner*—Cecilia Shen
*Attorney, Agent, or Firm*—Richard K. Jackson

[57] ABSTRACT

The compounds of the following structural formula posses useful anxiolytic, antidepressant, antipsychotic and learning and memory enhancement properties:

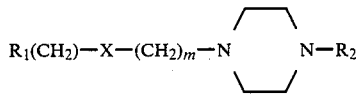

in which
  $R^1$ is 3-noradamantyl;
  n is 0 or 1;
  X is $-CO_2-$, $-O_2C-$ or $-OCO_2-$;
  m is 1, 2, 3, 4, or 5;
and
  $R^2$ is phenyl, benzyl, pyridinyl, pyrimidinyl, pyrazinyl or substituted phenyl or benzyl in which the substituent is alkyl, alkoxy, halo, cyano, nitro or trifluoromethyl;

or a pharmaceutically acceptable salt thereof.

6 Claims, No Drawings

NORADAMANTYL-CARBOXYLIC ACID PIPERAZINOALKYL ESTERS

BACKGROUND OF THE INVENTION

Derwent Abstract 85-000957/01 of German Application No. 3,321,969 discloses 1-pyrimidyl-4-substituted piperazine derivatives which possess a broad variety of CNS activity including anxiolytic and antidepressant properties. Netherlands Pat. No. 7,017,031 discloses 8-(heteroarylpiperazinylalkyl)-8-azaspiro[4,5]decane-7,9-diones as tranquilizers. U.S. Pat. No. 4,640,921 (Derwent Abstract 87-049798/07) discloses the use of the buspirones of the Netherlands patent in the treatment of sexual dysfunction in anxious patients. The anxiolytic activity of buspirone-like compounds has been attributed to their selective activation of a serotonin (5-hydroxytryptamine; 5-HT) subtype receptor designated the $5\text{-}HT_{1A}$ receptor. U.S. Pat. No. 4,202,898 discloses the treatment of anxiety and depression with aromatically substituted piperazine derivatives. $5\text{-}HT_2$ antagonists, such as Ritanserin, lack $5\text{-}HT_{1A}$ affinity but demonstrate clinical efficacy as anxiolytic-antidepressant agents (Barone et al., Drug Clin. Pharm., 20, 770, 1986).

DESCRIPTION OF THE INVENTION

In accordance with this invention there is provided a group of novel compounds, some of which exhibit selective serotonin $5HT_{1A}$ receptor affinity which characterizes them as antidepressants and anxiolytics; some of which exhibit both $5HT_{1A}$ receptor affinity and dopamine D2 receptor binding which characterizes them as antipsychotic agents with anxiolytic/antidepressant elements; and some of which exhibit very good selective affinity for muscarinic acetylcholine M1 receptor sites over the M2 receptor sites, characterizing them as useful in treatment of diseases characterized by cholinergic hypofunction, such as senile dementia of the Alzheimer's type, Huntingdon's chorea, Parkinson's syndrome and stroke. The compounds of this invention are of the following structural formula:

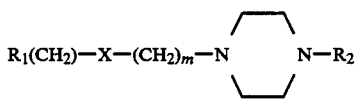

wherein
R$^1$ is 3-noradamantyl;
n is 0 or 1;
X is $-CO_2-$, $-O_2C-$ or $OCO_2-$;
m is 1, 2, 3, 4 or 5;
and
R$^2$ is phenyl, benzyl, pyridinyl, pyrimidinyl, pyrazinyl, or substituted phenyl or benzyl in which the substituent is alkyl of 1 to 6 carbon atoms, alkoxy of 1 to 6 carbon atoms, halo, cyano, nitro or trifluoromethyl.

The preferred compounds are those esters derived from noradamantane-3-carboxylic acid.

The pharmaceutically acceptable salts are conveniently derived by conventional means from such acids as hydrochloric, hydrobromic, sulfuric, phosphoric, methane sulfonic, nitric, p-toluene sulfonic, acetic, citric, maleic, succinic acid, and the like. The halogens embraced by the term halo are chlorine, bromine, iodine and fluorine, preferably chlorine, bromine or fluorine.

The compounds of this invention may be prepared by a variety of synthetic routes using conventional methods. For instance, noradamantane-3-carboxylic acid may be conveniently reacted with the appropriately substituted

in $CH_2Cl_2$ or $CHCl_3$ and in the presence of a suitable coupling agent conventionally employed in production of esters such as carbonyldiimidazole. Alternatively, an acid halide of noradamantane-3-carboxylic acid may be reacted with the desired hydroxyhaloalkane $-HO-(CH_2)_m-Br-$ in $CH_2Cl_2$ and the presence of a suitable base, such as triethylamine, followed by reacting the intermediate bromoalkylester with the desired aromatically or heteroaromatically substituted piperidine intermediate. The reverse esters are produced from the obvious reactants bearing transposed functional groups. The carbonates are produced from noradamantane-3-ol and the chloroformate of the appropriately substituted N-hydroxylalkylpiperazine.

The following examples illustrate, without limitation, the specific methods employed in production of a representative number of compounds embraced by this invention.

EXAMPLE 1

Hexahydro-2,5-methanopentalene-3a[1H]-carboxylic acid 2-[4-(2-pyrimidyl)-1-piperazinyl]ethyl ester To a stirred solution of hexahydro-2,5-methanopentalene-3a[1H]-carboxylic acid (1.0 g, $6.0 \times 10^{-3}$ mol) in 25 ml of chloroform under a dry nitrogen atmosphere, was added carbonyldiimidazole (0.98 g, $6.0 \times 10^{-3}$ mol). The resulting solution was stirred at ambient temperature for three hours, during which time a gas ($CO_2$) was evolved. A solution of 2-[1-(2-pyrimidyl)-4-piperazinyl]ethanol (1.25 g, $6.0 \times 10^{-3}$ mol) in 25 ml of chloroform was then added, and the resulting reaction mixture was stirred under nitrogen at ambient temperature for two days. The mixture was diluted to 150 ml with chloroform, washed with three-one hundred ml portions of water, dried over anhydrous sodium sulfate, and concentrated on a rotary evaporator. The desired product (TLC on silica using a 30% methanol in ethyl acetate solvent system, Rf=0.45) was isolated by gravity chromatography on silica gel and converted to the hydrochloride salt with isopropanolic HCl (1.76 g, 61% yield), mp.=219°-220° C.

Elemental Analysis for $C_{20}H_{28}N_4O_2 \cdot 2HCl$. Calc'd: C, 55.94; H, 7.04; N, 13.05. Found: C, 55.66; H, 7.14; N, 12.98.

EXAMPLE 2

Hexahydro-2,5-methanopentalene-3a[1H]-carboxylic acid 2-[4-(2-methoxyphenyl)-1-piperazinyl]ethyl ester To a stirred solution of hexahydro-2,5-methanopentalene-3a[1H]-carboxylic acid (0.6 g, $3.6 \times 10^{-3}$ mol) in 25 ml of chloroform un der a dry nitrogen atmosphere was added carbonyldiimidazole (0.58 g, $3.6 \times 10^{-3}$ mol).

The resulting solution was stirred at ambient temperature for three hours, during which time a gas ($CO_2$) was evolved. A solution of 2-[1-(2-methoxyphenyl)-4-piperazinyl]ethanol (0.86 g, $3.6 \times 10^{-3}$ mol) in 25 ml of chloroform was then added, and the resulting reaction mixture was stirred under nitrogen at ambient temperature for two days. The mixture was diluted to 150 ml with chloroform, washed with three-one hundred ml portions of water, dried over anhydrous sodium sulfate, and concentrated on a rotary evaporator. The desired product (TLC on silica using a 30% methanol in ethyl acetate solvent system, RF=0.60) was isolated by gravity chromatography on silica gel and converted to the hydrochloride salt with isopropanolic HCl (0.82 g, 44% yield), mp.=207°–208° C.

Elemental analysis for $C_{23}H_{32}N_2O_3 \cdot 2HCl$. Calc'd: C, 60.39; H, 7.49; N, 6.12. Found: C, 60.47; H, 7.58; N, 5.92.

EXAMPLE 3

Hexahydro-2,5-methanopentalene-3a[1H]-carboxylic acid 3-[4-(2-pyrimidyl)-1-piperazinyl]propyl ester To stirred solution of hexahydro-2,5-methanopentalene-3a[1H]-carboxylic acid (0.6 g, $3.6 \times 10^{-3}$ mol) in 25 ml of chloroform under a dry nitrogen atmosphere was added carbonyldiimidazole (0.58 g, $3.6 \times 10^{-3}$ mol). The resulting solution was stirred at ambient temperature for three hours, during which time a gas ($CO_2$) was evolved. A solution of 3-[1-(2-pyrimidyl)-4-piperazinyl]propanol (0.80 g, $3.6 \times 10^{-3}$ mol) in 25 ml of chloroform was then added, and the resulting reaction mixture was stirred under nitrogen at ambient temperature for two days. The mixture was diluted to 150 ml with chloroform, washed with three-one hundred ml portions of water, dried over anhydrous sodium sulfate, and concentrated on a rotary evaporator. The desired product (TLC on silica using a 30% methanol in ethyl acetate solvent system, Rf=0.48) was isolated by gravity chromatography on silica gel and converted to the hydrochloride salt with isopropanolic HCl (0.79 g, 51% yield), mp.=231°–232° C.

Elemental analysis for $C_{21}H_{30}N_4O_2 \cdot 2HCl \cdot H_2O$. Calc'd: C, 52.61; H, 7.14; N, 11.69. Found: C, 52.75; H, 7.10; N, 11.74.

EXAMPLE 4

Hexahydro-2,5-methanopentalene-3a[1H]carboxylic acid 3-[4-(2-methoxyphenyl)-1-piperazinyl]propyl ester To a stirred solution of hexahydro-2,5-methanopentalene-3a[1H]-carboxylic acid (0.6 g, $3.6 \times 10^{-3}$ mol) in 25 ml of chloroform under a dry nitrogen atmosphere was added carbonyldiimidazole (0.58 g, $3.6 \times 10^{-3}$ mol). The resulting solution was stirred at ambient temperature for three hours, during which time a gas ($CO_2$) was evolved. A solution of 3-[1-(2-methoxyphenyl)-4-piperazinyl]propanol (0.91 g, $3.6 \times 10^{-3}$ mol) in 25 ml of chloroform was then added, and the resulting reaction mixture was stirred under nitrogen at ambient temperature for two days. The mixture was diluted to 150 ml with chloroform, washed with three-one hundred ml portions of water, dried over anhydrous sodium sulfate, and concentrated on a rotary evaporator. The desired product (TLC on silica using a 30% methanol in ethyl acetate solvent system, Rf=0.52) was isolated by gravity chromatography on silica gel and converted to the hydrochloride salt with isopropanolic HCl (0.84 g, 50% yield), mp.=206°–207° C.

Elemental analysis for $C_{24}H_{34}N_2O_3 \cdot 2HCl$. Calc'd: C, 61.14; H, 7.70; N, 5.94. Found: C, 60.78; H, 7.77; N, 5.60.

The compounds of this invention are antidepressant, anxiolytic agents useful in the treatment of depression and/or anxiety as a singular, primary mental problem as well as secondary, attending problems such as sexual dysfunction. Some of the compounds possess sufficient dopaminergic activity to be useful in treating psychoses such as schizophrenia or paranoia. Examples of compounds with sufficient limbic $D_2$ (dopamine) receptor affinity to be considered to have an antipsychotic parameter are those demonstrating about 80% or more inhibition of $^3$H-spiroperidol binding to limbic brain tissue at 1 $\mu$M concentration of the test compound. The $D_2$ receptor affinity of representative compounds of this invention was determined by a modification of the test procedure of Fields et al., Brain Res. 136, 578 (1977) and Yamamura et al., eds., Neurotransmitter Receptor Binding, Raven Press, N.Y. (1978) as discussed in U.S. Pat. No. 4,636,563. The percentage reduction of $^3$H-spiroperidol binding at 1 $\mu$M concentration of test compound is reported, infra, and the inhibition constant (Ki) for the specific test compound is reported where available. Buspirone exhibits a Ki value of 78 nM against $^3$H-spiroperidol binding in this standard test procedure.

The serotoninergic properties of the compounds of this invention were established by the procedure of Hall et al., J. Neurochem. 44, 1685–1696 (1985) by demonstrating that representative compounds exemplified herein displace $^3$H-8-OH DPAT (dipropylaminotetralin) from the 5-HT$_{1A}$ serotonin receptor subtype. The results of this standard pharmacological procedure are reported, infra, as the percent inhibition at 1 $\mu$M or 100 nM concentration of test compound or by providing the inhibition constant Ki for the specific test compound where that calculation has been made from appropriate IC$_{50}$ values. Buspirone exhibits a Ki value of 10 nM (97% inhibition at 1 $\mu$M) in this test procedure.

The M1 muscarinic receptor binding properties of the compounds of this invention were established as follows:

Homogenized rat hippocampus tissue is suspended in 0.32M aqueous sucrose solution and centrifuged (747×g for 10 minutes at 4° C.) and the supernatent liquid is decanted and recentrifuged (18,677×g for 20 minutes at 4° C.). The resulting pellet is resuspended in the original volume of 0.32M aqueous sucrose. The sample is then diluted 1:2 in 10 mM Na$_2$HPO$_4$/KH$_2$PO$_4$ buffer (pH=7.4). A 100 $\mu$l sample of the buffered tissue suspension is incubated at 25° C. for 60 minutes in the dark with 10 $\mu$l of test compound or vehicle for control and [$^3$H] pirenzipine (0.5 nM, 0.04 $\mu$Ci) q.s. 1 milliliter with the buffer solution. Atropine sulfate (2 $\mu$M) is added to half the samples being processed. Binding is terminated by vacuum filtration onto Whatman GF/B filters which are washed three times with the buffer solution (3 ml/wash, 4° C.). The radioactivity of the filter-trapped material is determined by liquid scintillation spectroscopy and the IC$_{50}$ (50% inhibition of specific [$^3$H] PZ binding) is calculated for the test compound. Specific ]$^3$H] PZ binding is defined as total binding minus binding in the presence of 2 $\mu$M atropine sulfate.

The M2 receptor binding properties of the compounds of this invention were determined in the manner described for M1 receptor determinations with the following exceptions. Homogenized rat cerebellum tissue, diluted 1:3 in the above mentioned phosphate buffer, was employed for its M2 receptor sites and [$^3$H] quinuclidinyl benzilate (0.23 nM, 0.01 μCi) was employed as the muscarinic receptor ligand. The concentration of atropine sulfate used in the experiments was 100 μM. The assay tubes were incubated at 37° C. for 60 minutes.

| Affinity for 5-HT$_{1A}$ Receptor Sites | | |
|---|---|---|
| Compounds of Example | % Inhibition at 1 μM (Ki in nM) | % Inhibition at 100 nM |
| 1 | 93% (23 nM) | |
| 2 | 95% | |
| 3 | | 12% |
| 4 | 96% | |

| Affinity for D$_2$ Receptor Sites | |
|---|---|
| Compound of Example | % Inhibition at 1 μM |
| 1 | 47% |
| 2 | 100% |
| 3 | |
| 4 | 100% |

| Affinity for Muscarinic Acetylcholine Receptor Sites | | | |
|---|---|---|---|
| Compounds of Example | IC$_{50}$ for M1 | IC$_{50}$ for M2 | M2/M1 Ratio |
| 3 | 0.85 μM | 69 μM | 81 |

The muscarinic M2 receptor subtype serves to control presynaptic acetylcholine release. Activation of the M2 receptor inhibits acetylcholine release, thereby exerting a negative influence on learning and memory processes which are at least partially regulated by the central cholinergic system. The muscarinic M1 receptor subtype is localized on the postsynaptic nerve cell where activation provides direct enhancement of the central cholinergic function. Enhancement of the central cholinergic function by direct stimulation of the M1 muscarinic receptor subtype provides one method of treatment for the central cholinergic dysfunction attending senile dementia of the Alzheimer type (SDAT) as a primary manifestation. Therefore, compounds to be used in treatment of Alzheimer's disease and similar disease involving memory impairment and learning disabilities should exhibit selectivity for the M1 receptor over the M2 muscarinic receptor in the central nervous system. The compound produced in Example 3 epitomizes the desired selective property in this case.

In qualitatively evaluating the above data, high affinity values for 5-HT$_{1A}$ receptors correlate (by analogy with buspirone) with anxiolytic-antidepressant activity, while lower values reflect a lesser activity. High affinity values for D$_2$ receptor binding (greater than 80%) begin to show some antipsychotic activity.

Hence, the compounds of this invention are antidepressant/anxiolytic agents useful in the treatment of depression and in alleviating anxiety and in the case of the products of Examples 2 and 4, they have some meaningful antipsychotic activity which is useful in the treatment of psychoses such as paranoia and schizophrenia. Central cholinergic activity is evidenced by the product of Example 3, which establishes the compounds as useful in the treatment of SDAT, Huntingdon's chorea, and the like diseases attending cholinergic hypofunction. As such, the compounds of this invention may be administered to a patient in need thereof, either neat or with a conventional pharmaceutical carrier. The pharmaceutical carrier may be solid or liquid as suitable for oral or parenteral administration.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration the carrier can also be an oil ester such as ethyl oleate and isopropyl myristate. Steril liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is subdivided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or table itself, or it can be the appropriate number of any such compositions in package form.

The dosage to be used in the treatment of anxiety, depression, psychoses, senile dementia, stroke, etc. must be subjectively determined by the attending physician. The variables involved include the specific state of depression, anxiety or psychoses and the size, age and response pattern of the patient.

What is claimed is:

1. A compound of formula:

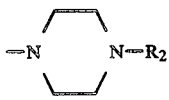

wherein
R¹ is 3-noradamantyl;
n is 0 or 1;
X is —CO₂—, —O₂C— or —OCO₂—;
m is 1, 2, 3, 4 or 5;
and R² is phenyl, benzyl, pyridinyl, pyrimidinyl, pyrazinyl, a substitued phenyl or benzyl in which the substituent is alkyl of 1 to 6 carbon atoms, alkoxy of 1 to 6 carbon atoms, halo, cyano, nitro or trifluoromethyl; or a pharmaceutically acceptable salt thereof.

2. A compound of claim 1 in which X is —CO₂—.

3. The compound of claim 1 which is hexahydro-2,5-methanopentalene-3a[1H]-carboxylic acid 2-[4-(2-pyrimidyl)-1-piperazinyl]ethyl ester.

4. The compound of claim 1 which is hexahydro-2,5-methanopentalene-3a[1H]-carboxylic acid 2-[4-(2-methoxyphenyl)-1-piperazinyl]ethyl ester.

5. The compound of claim 1 which is hexahydro-2,5-methanopentalene-3a[1H]-carboxylic acid 3-[4-(2-pyrimidyl)-1-piperazinyl]propyl ester.

6. The compound of claim 1 which is hexahydro-2,5-methanopentalene-3a[1H]-carboxylic acid 3-[4-(2-methoxyphenyl)-1-piperazinyl]propyl ester.

* * * * *